(12) United States Patent
Jacques et al.

(10) Patent No.: US 11,008,374 B2
(45) Date of Patent: May 18, 2021

(54) USES OF IL-15 ANTAGONISTS FOR THE TREATMENT OF AUTOIMMUNE AND INFLAMMATORY DISEASES

(71) Applicants: INSERM (Institut National de la Sante et de la Recherche Medicale), Paris (FR); Universite de Nantes, Nantes (FR); Centre National de la Recherche Scientifique (CNRS), Paris (FR); Universite D'Angers, Angers (FR)

(72) Inventors: Yannick Jacques, Nantes (FR); Erwan Mortier, Nantes (FR); Agnes Quemener, Nantes (FR); Ariane Plet, Nantes (FR)

(73) Assignees: INSERM (Institut National de la Santé et de la Recherche Médicale), Paris (FR); Université de Nantes, Nantes (FR); Centre National de la Recherche Scientifique (CNRS), Paris (FR); Université d'Angers, Angers (FR)

( * ) Notice: Subject to any disclaimer, the term of this patent is extended or adjusted under 35 U.S.C. 154(b) by 60 days.

(21) Appl. No.: 16/217,130

(22) Filed: Dec. 12, 2018

(65) Prior Publication Data

US 2019/0106472 A1  Apr. 11, 2019

Related U.S. Application Data

(62) Division of application No. 14/897,344, filed as application No. PCT/EP2014/063637 on Jun. 27, 2014, now Pat. No. 10,202,433.

(30) Foreign Application Priority Data

Jun. 27, 2013  (EP) .................................. 13305896

(51) Int. Cl.
*A61K 38/20* (2006.01)
*C07K 14/54* (2006.01)
*A61K 38/00* (2006.01)

(52) U.S. Cl.
CPC .......... *C07K 14/5443* (2013.01); *A61K 38/00* (2013.01); *C07K 2319/30* (2013.01)

(58) Field of Classification Search
None
See application file for complete search history.

(56) References Cited

U.S. PATENT DOCUMENTS

2003/0105295 A1* 6/2003 Strom .................... A61P 29/00
530/351
2003/0235586 A1* 12/2003 van de Winkel .... C07K 16/244
424/145.1

* cited by examiner

*Primary Examiner* — Dong Jiang
(74) *Attorney, Agent, or Firm* — W&C IP

(57) ABSTRACT

The present relates to interleukin 15 (IL-15) antagonists and uses thereof, in particular for the treatment of autoimmune diseases and inflammatory diseases. In particular, the present invention relates to an IL-15 mutant polypeptide having the amino acid sequence as set forth in SEQ ID NO:1 wherein the leucine residue at position 45 is substituted by an aspartic acid residue, the asparagines residue at position 65 is substituted by a lysine residue and the leucine residue at position 69 is substituted by an arginine residue.

Figure 1A:
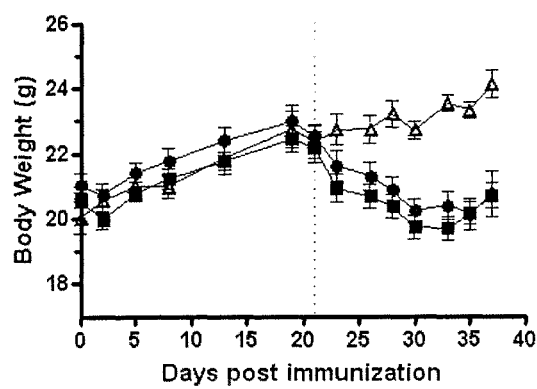
Figure 1B:
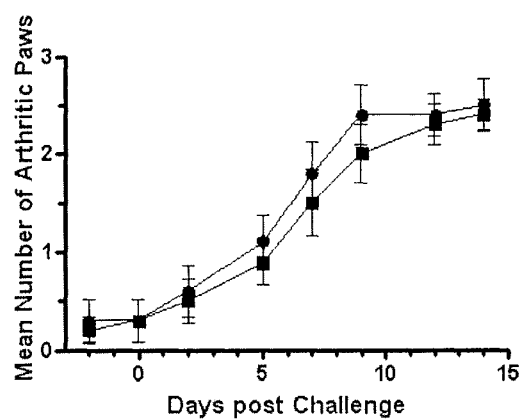
Figure 1C:
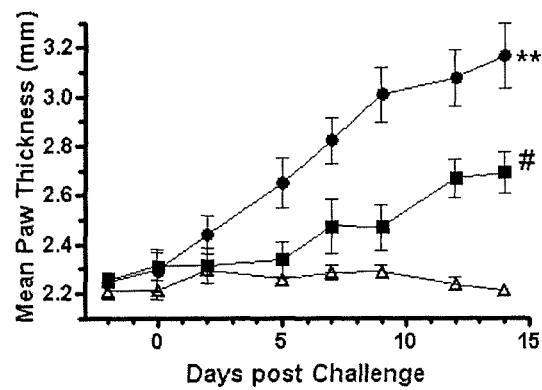

16 Claims, 4 Drawing Sheets
Specification includes a Sequence Listing.

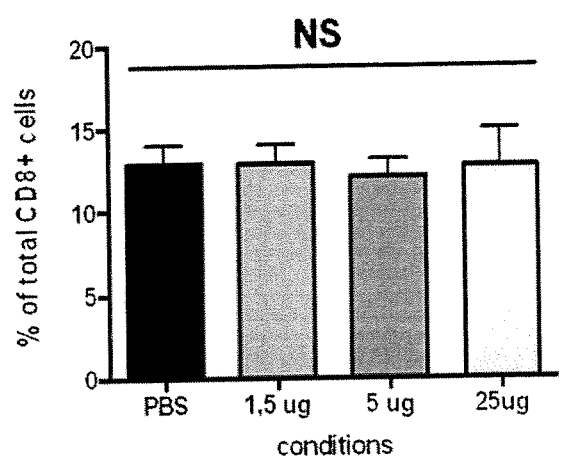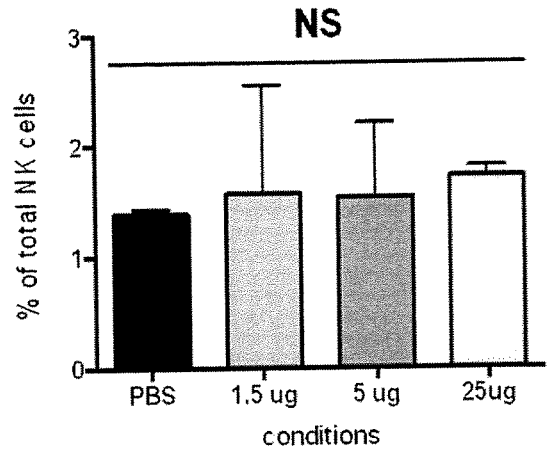
Figure 5A
Figure 5B

USES OF IL-15 ANTAGONISTS FOR THE TREATMENT OF AUTOIMMUNE AND INFLAMMATORY DISEASES

FIELD OF THE INVENTION

The present relates to interleukin 15 (IL-15) antagonists and uses thereof, in particular for the treatment of autoimmune diseases and inflammatory diseases.

BACKGROUND OF THE INVENTION

IL-15 is a 14-15 kDa cytokine simultaneously identified by two research groups as a T cell activating factor (Grabstein, K. H. et al., Science 1994, 264, 965-968; Burton, I. D. et al., Proc. Natl. Acad. Sci. USA 1994, 91, 4935-4939) and is involved in the differentiation and proliferation of NK and T cells. High levels of IL-15 expression have been associated to the pathogenesis of autoimmune and inflammatory diseases, like in Crohn's disease (Kirman I., Am. I. Gastroenterol. 1996, 91: 1789-1794), psoriasis (Rickert R., J. Immunol., 2000, 165: 2240-2250), leukemias (YamadaY Leukemia and Lymphoma 1999, 35: 37-4)5 and rheumatoid arthritis (RA) (McInnes I. B., Immunology Today 1998, 19: 75-79; Graft rejection (Pavlakis M, transplantation 1996, Manfro R C., Transplant Proc. 1997). Accordingly IL-15 antagonists could be a potential therapeutic to treat inflammatory diseases and several IL-15 antagonists have been described in the prior art. For example Ferrari-Lacraz S. et al. described an IL-15 antagonist consisting of an IL-15 mutant fused to a Fc domain of an immunoglobulin and demonstrated that said antagonist could be useful for the treatment of rheumatoid arthritis (Ferrari-Lacraz S, Zanelli E, Neuberg M, Donskoy E, Kim Y S, Zheng X X, Hancock W W, Maslinski W, Li X C, Strom T B, Moll T. Targeting IL-15 receptor-bearing cells with an antagonist mutant IL-15/Fc protein prevents disease development and progression in murine collagen-induced arthritis. J Immunol. 2004 Nov. 1; 173(9):5818-26). Bemard et al. identified in 2004 two sequences of the IL-15 molecule for binding to IL15-Ralpha. Those sequences comprise amino acids 44 to 52 and 64 to 68 in the mature protein, and they also described muteins that could act as agonists or antagonists of IL-15 (Bernard I. et al. I Biol Chem 2004, 279: 24313-24322). Furthermore Pedreau H. et al. (Harmonie Perdreau; Ariane Plet; Yannick Jacques; Université de Nantes. Unité de Formation et de Recherche de Médecine et des Techniques Médicales.; École doctorale 502 Biologie-Santé(Nantes-Angers). Biologie de l'interleukine-15: de son ADN à ses voies de signalisation. 2010; Thèse de doctorat: Médecine. Biologie, médecine et santé. Immunologie: Nantes: 2010) described two IL-15 muteins for the production in baculovirus.

SUMMARY OF THE INVENTION

The present relates to interleukin 15 (IL-15) antagonists and uses thereof, in particular for the treatment of autoimmune diseases and inflammatory diseases.

DETAILED DESCRIPTION OF THE INVENTION

The inventors have designed a new IL-15 mutant molecule that can be fused to a Fc fragment. The mutations are located on the IL-15 interface that interacts with the IL-15Rβ chain in order to prevent IL-15 signaling both through the IL-15Rβ/γ heterodimeric receptors and the IL-15Rββ homodimeric receptors that are putative receptors for IL-2 and IL-15. Accordingly the strategy to use an IL-15 antagonist that targets the IL-15Rβ chain rather than the common γ chain, would therefore be more efficient because the skilled artisan can anticipate that, by blocking all possible forms of IL-15 receptors (IL15Rα/β/γ, IL-15Rβ/γ and IL-15Rβ/β), the molecule would block more efficiently both CD8 T cells and NK cells action.

The present invention relates to an IL-15 mutant polypeptide having the amino acid sequence as set forth in SEQ ID NO:1 wherein the leucine residue at position 45 is substituted by an aspartic acid residue, the asparagine residue at position 65 is substituted by a lysine residue and the leucine residue at position 69 is substituted by an arginine residue.

SEQ ID NO: 1: IL-15 (*Homo sapiens*)
NWVNVISDLK KIEDLIQSMH IDATLYTESD VHPSCKVTAM
KCFL<u>L</u>ELQVI SLESGDASIH DTVE<u>N</u>LIIL<u>A</u> NNSLSSNGNV
TESGCKECEE LEEKNIKEFL QSFVHIVQMF INTS The present invention also relates to a fusion protein consisting of an IL-15 mutant polypeptide according to the invention fused to a heterologous polypeptide (i.e., a polypeptide that is not IL-15 or a mutant thereof).

As used herein, a "fusion protein" comprises all or part (typically biologically active) of a polypeptide of the invention operably linked to a heterologous polypeptide (i.e., a polypeptide other than the same polypeptide of the invention). Within the fusion protein, the term "operably linked" is intended to indicate that the polypeptide of the invention and the heterologous polypeptide are fused in-frame to each other. The heterologous polypeptide can be fused to the N-terminus or C-terminus of the polypeptide of the invention. Typically, the heterologous polypeptide is particularly suitable for increasing the circulating half-life of the IL-15 mutant polypeptide in vivo.

In a particular embodiment, the fusion protein is an immunoadhesin. As used herein, the term "immunoadhesin" designates antibody-like molecules which combine the binding specificity of the IL-15 mutant polypeptide of the invention with the effector functions of immunoglobulin constant domains. In some embodiments, the immunoglobulin constant domain sequence in the immunoadhesin may be obtained from any immunoglobulin, such as IgG-1, IgG-2, IgG-3, or IgG-4 subtypes, IgA (including IgA-1 and IgA-2), IgE, IgD or IgM. In some embodiments, the immunoglobulin sequence typically, but not necessarily, is an immunoglobulin constant domain (Fc region). Immunoadhesins can possess many of the valuable chemical and biological properties of human antibodies. Since immunoadhesins can be constructed from a human protein sequence with a desired specificity linked to an appropriate human immunoglobulin hinge and constant domain (Fc) sequence, the binding specificity of interest can be achieved using entirely human components. Such immunoadhesins are minimally immunogenic to the patient, and are safe for chronic or repeated use. The artisan skilled in the art can easily select the most appropriate Fc domain (Chan A C, Carter P J. Therapeutic antibodies for autoimmunity and inflammation. Nat Rev Immunol. 2010 May; 10(5):301-16. doi: 10.1038/nri2761. Review). In a particular embodiment, the Fc region includes or not a mutation that inhibits complement fixation and/or Fc receptor binding (Zheng et al, Transplantation. 2006 Jan. 15; 81(1):109-16).

In a particular embodiment, the Fc region is a native sequence Fc region. In a particular embodiment, the Fc region is a variant Fc region. In still another embodiment, the Fc region is a functional Fc region. As used herein, the term "Fc region" is used to define a C-terminal region of an immunoglobulin heavy chain, including native sequence Fc regions and variant Fc regions. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof.

In some embodiments, the adhesion portion and the immunoglobulin sequence portion of the immunoadhesin are linked by a minimal linker. As used herein, the term "linker" refers to a sequence of at least one amino acid that links the adhesion portion and the immunoglobulin sequence portion. Such a linker may be useful to prevent steric hindrances. In some embodiments, the linker has 4; 5; 6; 7; 8; 9; 10; 11; 12; 13; 14; 15; 16; 17; 18; 19; 20; 21; 22; 23; 24; 25; 26; 27; 28; 29; 30 amino acid residues. However, the upper limit is not critical but is chosen for reasons of convenience regarding e.g. biopharmaceutical production of such polypeptides. The linker sequence may be a naturally occurring sequence or a non-naturally occurring sequence. If used for therapeutical purposes, the linker is preferably non-immunogenic in the subject to which the immunoadhesin is administered. One useful group of linker sequences are linkers derived from the hinge region of heavy chain antibodies as described in WO 96/34103 and WO 94/04678. Other examples are poly-alanine linker sequences. Further preferred examples of linker sequences are Gly/Ser linkers of different length including (gly4ser)3 (SEQ ID NO:10), (gly4ser)4 (SEQ ID NO:11), (gly4ser) (SEQ ID NO:12), (gly3ser) (SEQ ID NO:13), gly3 (SEQ ID NO:14), and (gly3ser2)3 (SEQ ID NO:15).

```
                                        SEQ ID NO: 10
(GGGGS GGGGS GGGGS)

SEQ ID NO: 11
(GGGGS GGGGS GGGGS GGGGS)

SEQ ID NO: 12
(GGGGS)

SEQ ID NO: 13
(GGS)

SEQ ID NO: 14
(GGG)

SEQ ID NO: 15
(GGGSS GGGSS GGGSS)
```

In a particular embodiment, the fusion protein according to the invention has the amino acid sequence selected from the group consisting of SEQ ID NO:2, SEQ ID NO:3, SEQ ID NO:4, SEQ ID NO:7, SEQ ID NO:8 and SEQ ID NO:9.

SEQ ID NO: 2: IL-15-IgG1Fc (Murine)
NWVNVISDLKKIEDLIQSMHIDATLYTESDVHPSCKVTAMKCFLDELQVI

SLESGDASIHDTVEKLIIRANNSLSSNGNVTESGCKECEELEEKNIKEFL

QSFVHIVQMFINTSSGCKPCICTVPEVSSVFIFPPKPKDVLTITLTPKVT

CVVVDISKDDPEVQFSWFVDDVEVHTAQTQPREEQFNSTFRSVSELPIMH

QDWLNGKEFKCRVNSAAFPAPIEKTISKTKGRPKAPQVYTIPPPKEQMAK

DKVSLTCMITDFFPEDITVEWQWNGQPAENYKNTQPIMDTDGSYFVYSKL

NVQKSNWEAGNTFTCSVLHEGLHNHHTEKSLSHSPGK

SEQ ID NO: 3 IL-15-IgG1Fc (Human)
NWVNVISDLKKIEDLIQSMHIDATLYTESDVHPSCKVTAMKCFLDELQVI

SLESGDASIHDTVEKLIIRANNSLSSNGNVTESGCKECEELEEKNIKEFL

QSFVHIVQMFINTSDKTHTCPPCPAPELLGGPSVFLFPPKPKDTLMISRT

PEVTCVVVDVSHEDPEVKFNWYVDGVEVHNAKTKPREEQYNSTYRVVSVL

TVLHQDWLNGKEYKCKVSNKALPAPIEKTISKAKGQPREPQVYTLPPSRE

EMTKNQVSLTCLVKGFYPSDIAVEWESNGQPENNYKTTPPVLDSDGSFFL

YSKLTVDKSRWQQGNVFSCSVMHEALHNHYTQKSLSLSPGK

SEQ ID NO: 4 IL-15-IgG2Fc (Human)
NWVNVISDLKKIEDLIQSMHIDATLYTESDVHPSCKVTAMKCFLDELQVI

SLESGDASIHDTVEKLIIRANNSLSSNGNVTESGCKECEELEEKNIKEFL

QSFVHIVQMFINTSVECPPCPAPPVAGPSVFLFPPKPKDTLMISRTPEVT

CVVVDVSHEDPEVQFNWYVDGMEVHNAKTKPREEQFNSTFRVVSVLTVVH

QDWLNGKEYKCKVSNKGLPAPIEKTISKTKGQPREPQVYTLPPSREEMTK

NQVSLTCLVKGFYPSDIAVEWESNGQPENNYKTTPPMLDSDGSFFLYSKL

TVDKSRWQQGNVFSCSVMHEALHNHYTQKSLSLSPGK

SEQ ID NO: 7 IL-15-Linker-IgG1Fc (Murine)
NWVNVISDLKKIEDLIQSMHIDATLYTESDVHPSCKVTAMKCFLDELQVI

SLESGDASIHDTVEKLIIRANNSLSSNGNVTESGCKECEELEEKNIKEFL

QSFVHIVQMFINTS*GGGGSGGGGSGGGGS*SGCKPCICTVPEVSSVFIFPP

KPKDVLTITLTPKVTCVVVDISKDDPEVQFSWFVDDVEVHTAQTQPREEQ

FNSTFRSVSELPIMHQDWLNGKEFKCRVNSAAFPAPIEKTISKTKGRPKA

PQVYTIPPPKEQMAKDKVSLTCMITDFFPEDITVEWQWNGQPAENYKNTQ

PIMDTDGSYFVYSKLNVQKSNWEAGNTFTCSVLHEGLHNHHTEKSLSHSP

GK

SEQ ID NO: 8 IL-15-Linker-IgG1Fc (Human)
NWVNVISDLKKIEDLIQSMHIDATLYTESDVHPSCKVTAMKCFLDELQVI

SLESGDASIHDTVEKLIIRANNSLSSNGNVTESGCKECEELEEKNIKEFL

QSFVHIVQMFINTS*GGGGSGGGGSGGGGS*DKTHTCPPCPAPELLGGPSVF

LFPPKPKDTLMISRTPEVTCVVVDVSHEDPEVKFNWYVDGVEVHNAKTKP

REEQYNSTYRVVSVLTVLHQDWLNGKEYKCKVSNKALPAPIEKTISKAKG

QPREPQVYTLPPSREEMTKNQVSLTCLVKGFYPSDIAVEWESNGQPENNY

KTTPPVLDSDGSFFLYSKLTVDKSRWQQGNVFSCSVMHEALHNHYTQKSL

SLSPGK

SEQ ID NO: 9 IL-15 Linker-IgG2Fc (Human)
NWVNVISDLKKIEDLIQSMHIDATLYTESDVHPSCKVTAMKCFLDELQVI

SLESGDASIHDTVEKLIIRANNSLSSNGNVTESGCKECEELEEKNIKEFL

QSFVHIVQMFINTS*GGGGSGGGGSGGGGS*VECPPCPAPPVAGPSVFLFPP

KPKDTLMISRTPEVTCVVVDVSHEDPEVQFNWYVDGMEVHNAKTKPREEQ

FNSTFRVVSVLTVVHQDWLNGKEYKCKVSNKGLPAPIEKTISKTKGQPRE

PQVYTLPPSREEMTKNQVSLTCLVKGFYPSDIAVEWESNGQPENNYKTTP

-continued
PMLDSDGSFFLYSKLTVDKSRWQQGNVFSCSVMHEALHNHYTQKSLSLSP
GK

The polypeptides and fusion proteins of the invention may be produced by any technique known per se in the art, such as, without limitation, any chemical, biological, genetic or enzymatic technique, either alone or in combination. Knowing the amino acid sequence of the desired sequence, one skilled in the art can readily produce said polypeptides, by standard techniques for production of polypeptides. For instance, they can be synthesized using well-known solid phase method, preferably using a commercially available peptide synthesis apparatus (such as that made by Applied Biosystems, Foster City, Calif.) and following the manufacturer's instructions. Alternatively, the polypeptides and fusions proteins of the invention can be synthesized by recombinant DNA techniques as is now well-known in the art. For example, these fragments can be obtained as DNA expression products after incorporation of DNA sequences encoding the desired (poly)peptide into expression vectors and introduction of such vectors into suitable eukaryotic or prokaryotic hosts that will express the desired polypeptide, from which they can be later isolated using well-known techniques.

Polypeptides and fusions proteins of the invention can be used in an isolated (e.g., purified) form or contained in a vector, such as a membrane or lipid vesicle (e.g. a liposome).

In specific embodiments, it is contemplated that polypeptides and fusions proteins of the invention may be modified in order to improve their therapeutic efficacy. Such modification of therapeutic compounds may be used to decrease toxicity, increase circulatory time, or modify biodistribution. For example, the toxicity of potentially important therapeutic compounds can be decreased significantly by combination with a variety of drug carrier vehicles that modify biodistribution. A strategy for improving drug viability is the utilization of water-soluble polymers. Various water-soluble polymers have been shown to modify biodistribution, improve the mode of cellular uptake, change the permeability through physiological barriers; and modify the rate of clearance from the body. To achieve either a targeting or sustained-release effect, water-soluble polymers have been synthesized that contain drug moieties as terminal groups, as part of the backbone, or as pendent groups on the polymer chain. For example, Pegylation is a well established and validated approach for the modification of a range of polypeptides. The benefits include among others: (a) markedly improved circulating half-lives in vivo due to either evasion of renal clearance as a result of the polymer increasing the apparent size of the molecule to above the glomerular filtration limit, and/or through evasion of cellular clearance mechanisms; (b) reduced antigenicity and immunogenicity of the molecule to which PEG is attached; (c) improved pharmacokinetics; (d) enhanced proteolytic resistance of the conjugated protein; and (e) improved thermal and mechanical stability of the PEGylated polypeptide.

Another object of the invention relates to an isolated, synthetic or recombinant nucleic acid encoding for a polypeptide or a fusion protein of the invention.

Typically, said nucleic acid is a DNA or RNA molecule, which may be included in any suitable vector, such as a plasmid, cosmid, episome, artificial chromosome, phage or a viral vector. The terms "vector", "cloning vector" and "expression vector" mean the vehicle by which a DNA or RNA sequence (e.g. a foreign gene) can be introduced into a host cell, so as to transform the host and promote expression (e.g. transcription and translation) of the introduced sequence.

So, another object of the invention relates to a vector comprising a nucleic acid of the invention.

Such vectors may comprise regulatory elements, such as a promoter, enhancer, terminator and the like, to cause or direct expression of said polypeptide upon administration to a subject. The vectors may further comprise one or several origins of replication and/or selectable markers. The promoter region may be homologous or heterologous with respect to the coding sequence, and provide for ubiquitous, constitutive, regulated and/or tissue specific expression, in any appropriate host cell, including for in vivo use. Examples of promoters include bacterial promoters (T7, pTAC, Trp promoter, etc.), viral promoters (LTR, TK, CMV-IE, etc.), mammalian gene promoters (albumin, PGK, etc), and the like. Examples of plasmids include replicating plasmids comprising an origin of replication, or integrative plasmids, such as for instance pUC, pcDNA, pBR, and the like. Examples of viral vector include adenoviral, retroviral, herpes virus and AAV vectors. Such recombinant viruses may be produced by techniques known in the art, such as by transfecting packaging cells or by transient transfection with helper plasmids or viruses. Typical examples of virus packaging cells include PA317 cells, PsiCRIP cells, GPenv+ cells, 293 cells, etc. Detailed protocols for producing such replication-defective recombinant viruses may be found for instance in WO 95/14785, WO 96/22378, U.S. Pat. Nos. 5,882,877, 6,013,516, 4,861,719, 5,278,056 and WO 94/19478.

Another object of the present invention relates to a cell which has been transfected, infected or transformed by a nucleic acid and/or a vector according to the invention. The term "transformation" means the introduction of a "foreign" (i.e. extrinsic or extracellular) gene, DNA or RNA sequence to a host cell, so that the host cell will express the introduced gene or sequence to produce a desired substance, typically a protein or enzyme coded by the introduced gene or sequence. A host cell that receives and expresses introduced DNA or RNA has been "transformed".

The nucleic acids of the invention may be used to produce a recombinant polypeptide or fusion protein of the invention in a suitable expression system. The term "expression system" means a host cell and compatible vector under suitable conditions, e.g. for the expression of a protein coded for by foreign DNA carried by the vector and introduced to the host cell.

Common expression systems include *E. coli* host cells and plasmid vectors, insect host cells and Baculovirus vectors, and mammalian host cells and vectors. Other examples of host cells include, without limitation, prokaryotic cells (such as bacteria) and eukaryotic cells (such as yeast cells, mammalian cells, insect cells, plant cells, etc.). Specific examples include *E. coli, Kluyveromyces* or *Saccharomyces* yeasts, mammalian cell lines (e.g., Vero cells, CHO cells, 3T3 cells, COS cells, etc.) as well as primary or established mammalian cell cultures (e.g., produced from lymphoblasts, fibroblasts, embryonic cells, epithelial cells, nervous cells, adipocytes, etc.).

The present invention also relates to a method for producing a recombinant host cell expressing a polypeptide or a fusion protein of the invention, said method comprising the steps consisting of: (i) introducing in vitro or ex vivo a recombinant nucleic acid or a vector as described above into a competent host cell, (ii) culturing in vitro or ex vivo the recombinant host cell obtained and (iii), optionally, selecting the cells which express and/or secrete the polypeptide or fusion protein of the invention. Such recombinant host cells can be used for the production of polypeptides and fusions proteins of the present invention.

The invention further relates to a method of producing a polypeptide or a fusion protein of the invention, which method comprises the steps consisting of: (i) culturing a transformed host cell according to the invention under conditions suitable to allow expression of said polypeptide or fusion protein; and (ii) recovering the expressed polypeptide or fusion protein.

In some embodiment, the present invention relates to an IL-15 antagonist consisting of a dimer of the fusion protein of the invention. The IL-15 antagonist according to the invention is obtainable by a host cell transformed with a nucleic acid according encoding for a fusion protein of the invention. Typically the IL-15 antagonist according to the invention may be produced according to the protocol described in EXAMPLE 1.

The polypeptide, fusion protein and antagonist of the invention are particularly suitable for therapeutic purposes including the treatment of autoimmune diseases and inflammatory diseases.

Accordingly the present invention relates to a method of suppressing the immune response in a patient by administering a dose of a polypeptide, a fusion protein or an antagonist of the invention, and thereby modulates IL-15 dependent immune responses.

This method may be used to treat a patient who is suffering from an autoimmune disease, including but not limited to the following: (1) a rheumatic disease such as rheumatoid arthritis, systemic lupus erythematosus, Sjogren's syndrome, scleroderma, mixed connective tissue disease, dermatomyositis, polymyositis, Reiter's syndrome or Behcet's disease (2) type II diabetes (3) an autoimmune disease of the thyroid, such as Hashimoto's thyroiditis or Graves' Disease (4) an autoimmune disease of the central nervous system, such as multiple sclerosis, myasthenia gravis, or encephalomyelitis (5) a variety of phemphigus, such as phemphigus vulgaris, phemphigus vegetans, phemphigus foliaceus, Senear-Usher syndrome, or Brazilian phemphigus, (6) psoriasis, and (7) inflammatory bowel disease (e.g., ulcerative colitis or Crohn's Disease).

The administration of the polypeptide, the fusion protein or the antagonist of the invention may also be useful in the treatment of acquired immune deficiency syndrome (AIDS).

Another credible use for the polypeptide, the fusion protein or the antagonist of the invention includes the treatment of late phase HTLV (human T-cell lymphotrophic virus) I-induced adult T-cell leukemia-lymphoma, See Burton et al., Proc. Natl. Acad. Sci., 91:4935 (1994).

Similarly, the method may be used to treat a patient who has received a transplant of biological materials, such as an organ, tissue, or cell transplant. For example, the polypeptide, the fusion protein or the antagonist of the invention may be particularly suitable, in promoting graft survival (allograft or xenograft) and in treating patients with graft versus host disease.

Typically, the polypeptide, the fusion protein or the antagonist of the invention is typically administered in a therapeutically effective amount. By a "therapeutically effective amount" is meant a sufficient amount of the fusion protein or the antagonist of the invention to treat and/or to prevent the disease at a reasonable benefit/risk ratio applicable to any medical treatment. It will be understood that the total daily usage of the compounds and compositions of the present invention will be decided by the attending physician within the scope of sound medical judgment. The specific therapeutically effective dose level for any particular patient will depend upon a variety of factors including the disease being treated and the severity of the disease; activity of the specific compound employed; the specific composition employed, the age, body weight, general health, sex and diet of the patient; the time of administration, route of administration, and rate of excretion of the specific compound employed; the duration of the treatment; drugs used in combination or coincidental with the specific polypeptide employed; and like factors well known in the medical arts. For example, it is well known within the skill of the art to start doses of the compound at levels lower than those required to achieve the desired therapeutic effect and to gradually increase the dosage until the desired effect is achieved. However, the daily dosage of the products may be varied over a wide range from 0.01 to 1,000 mg per adult per day. Preferably, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the patient to be treated. A medicament typically contains from about 0.01 mg to about 500 mg of the active ingredient, preferably from 1 mg to about 100 mg of the active ingredient. An effective amount of the drug is ordinarily supplied at a dosage level from 0.0002 mg/kg to about 20 mg/kg of body weight per day, especially from about 0.001 mg/kg to 7 mg/kg of body weight per day.

A further object of the invention relates to pharmaceutical compositions comprising a polypeptide, a fusion protein or an antagonist of the invention for the prevention or treatment of atherosclerosis.

"Pharmaceutically" or "pharmaceutically acceptable" refer to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

The polypeptide, the fusion protein or the antagonist of the invention may be combined with pharmaceutically acceptable excipients, and optionally sustained-release matrices, such as biodegradable polymers, to form therapeutic compositions.

In the pharmaceutical compositions of the present invention for oral, sublingual, subcutaneous, intramuscular, intravenous, transdermal, local or rectal administration, the active principle, alone or in combination with another active principle, can be administered in a unit administration form, as a mixture with conventional pharmaceutical supports, to animals and human beings. Suitable unit administration forms comprise oral-route forms such as tablets, gel capsules, powders, granules and oral suspensions or solutions, sublingual and buccal administration forms, aerosols, implants, subcutaneous, transdermal, topical, intraperitoneal, intramuscular, intravenous, subdermal, transdermal, intrathecal and intranasal administration forms and rectal administration forms.

Preferably, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi.

Solutions comprising compounds of the invention as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The polypeptide, the fusion protein or the antagonist of the invention can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active polypeptides in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion. Some variation in dosage will necessarily occur depending on the condition of the subject being treated. The person responsible for administration will, in any event, determine the appropriate dose for the individual subject.

The polypeptide, the fusion protein or the antagonist of the invention may be formulated within a therapeutic mixture to comprise about 0.0001 to 1.0 milligrams, or about 0.001 to 0.1 milligrams, or about 0.1 to 1.0 or even about 10 milligrams per dose or so. Multiple doses can also be administered.

In addition to the compounds of the invention formulated for parenteral administration, such as intravenous or intramuscular injection, other pharmaceutically acceptable forms include, e.g. tablets or other solids for oral administration; liposomal formulations; time release capsules; and any other form currently used.

The invention will be further illustrated by the following figures and examples. However, these examples and figures should not be interpreted in any way as limiting the scope of the present invention.

FIGURES

FIG. 1A-D. IL-15AN-Fc inhibited the development of CIA. Collagen-primed DBA/1 mice were randomly divided into groups of 10, challenged on day 21, and given 14 daily i.p. injections of 1.5 µg of IL-15AN-Fc (■) or control mouse IgG2A (●) starting on day 22. Mice were monitored every two or three days for body weight and disease progression, which was quantified as body weight (A), mean number of arthritic paws (B), mean paw thickness (C) and mean clinical score (D). Values are mean±SEM. In A, the vertical line indicates the day of challenge. In C, mean paw thickness curve of 5 healthy mice (Δ) was reported. **P<0.01 versus healthy, #P<0.05 versus mouse IgG2a, Newman Keuls multiple comparison test.

Figure 2:
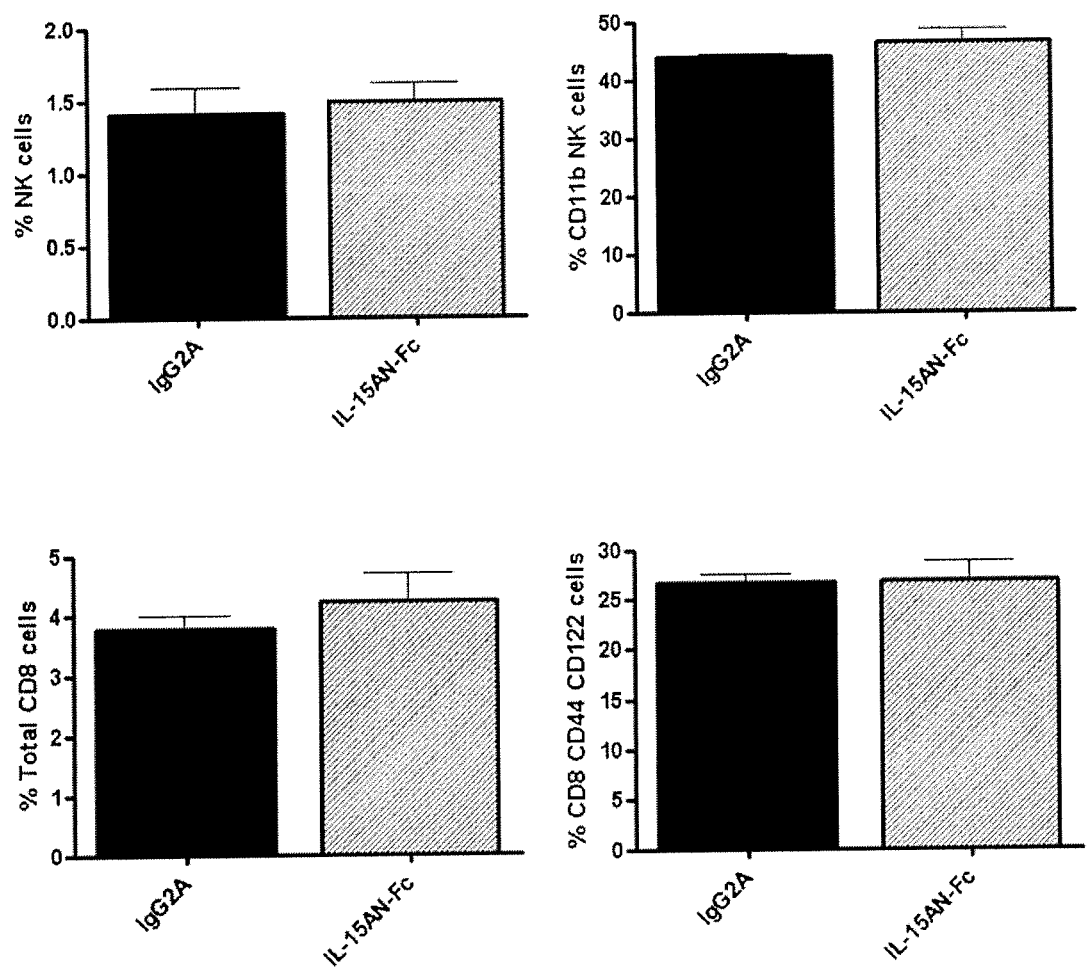

FIG. 2. IL-15AN-Fc treatment did not modify splenic NK and CD8+ T cells. The isolated splenic lymphocytes of mice were stained using either FITC-conjugated anti-mouse CD3e mAb, APC-conjugated anti-mouse NKp46 mAb, FITC-conjugated anti-mouse CD11b mAb and phycoerythrin(PE)-conjugated anti-mouse CD27 (BD Pharmingen), or FITC-conjugated anti-mouse CD3e mAb, APC-conjugated anti-mouse CD8 mAb, PE-conjugated anti-mouse CD122 mAb and FITC-conjugated anti mouse CD44 mAb and then analyzed using flow cytometry.

FIG. 3A-D. IL-15AN-Fc is effective in preventing disease progression in mice with established arthritis. After intradermal immunization and i.p. challenge with CII, mice were monitored daily for arthritis development. Treatment with either IL-15AN-Fc (■) or control IgG2a (●) (1.5 µg/mouse/day) was initiated as soon as a disease severity of at least 1 was scored in individual animals. The treatment was continued for 14 days. Mice were monitored everyday for body weight and disease progression, which was quantified as body weight (A), mean number of arthritic paws (B), mean paw thickness (C) and mean clinical score (D). Values are mean±SEM. In A, the vertical line indicates the day of challenge. In C, mean paw thickness curve of 3 healthy mice (Δ) was reported. In B, C and D, ***P<0.001 for IL-15AN-Fc versus IgG2a, Mann-Whitney test.

Figure 4:
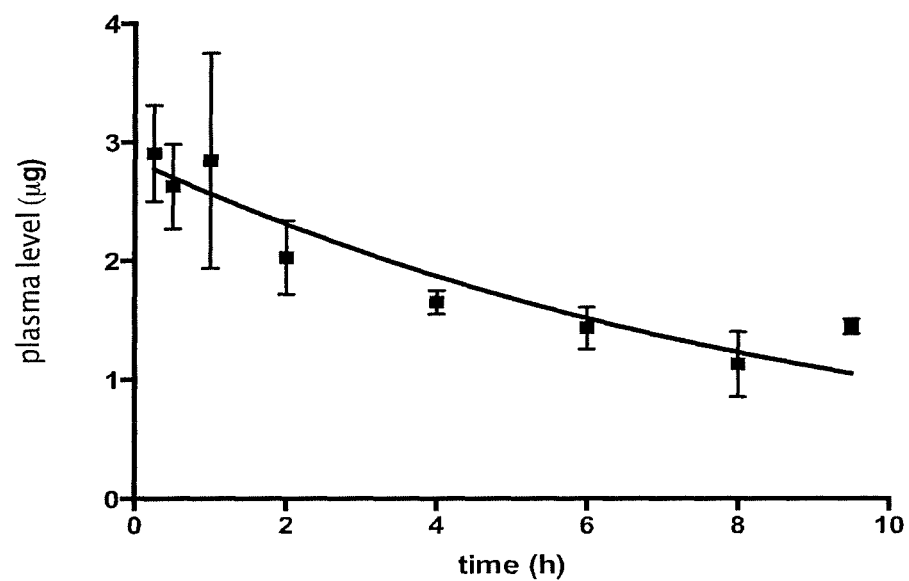

FIG. 4: pharmacokinetic of IL-15AN-Fc. Male C57BL/6 mice received one intravenous injection of 10 mg of IL-15AN-Fc, the blood was collected and IL-15AN-Fc concentration was measured every 2 hours (n=3).

FIG. 5A-B: Effect of IL-15AN-Fc on NK and T cells homeostasis. Flow cytometry analysis of (A) $CD3^+$ $CD8^+$ T and (B) $CD3^-$ $NK1.1^+$ populations in spleen. Student t test was used to compare between conditions; ns: not significant.

EXAMPLE 1

Material & Methods

Expression and Purification of IL-15AN-Fc Fusion Protein

IL-15 antagonist was designed to hold the two antagonistic point mutations N65K and L69R, generated with the Quick change site-directed mutagenesis kit (Stratagene, La Jolla, USA), to abrogate the binding of IL-15 to the β subunit of the receptor. To increase IL-15 expression, an AT-rich stretch present at the 3'end of the coding sequence was PCR-mutated without amino-acid change, using the 5' phosphorylated oligos: antisens oligo 5'-CTCCTT-GATGTTCTTCTCCTCCAGTTCCTCAC-3' (SEQ ID NO:5) and sens oligo 5'-TTCCTGCAGAGCTTCGTACAT-ATTGTCCAAATGTTCATC-3' (SEQ ID NO:6). To increase IL-15 solubility without notably changing IL-15 biological activity, leucine 45 was PCR-switched into aspartic acid. Moreover, IL-15 antagonist triple-mutant was fused to a mouse engineered IgG2a Fc region, mutated on amino acids critical for FcγRs and C1q binding, and expression driven by IL-2 signal peptide (pFuse-mIgG2Aa1-Fc2, Invivogen, San Diego). IL-15 DNA fragment was ligated between the EcoR1 and NcoI sites of the pFuse plasmid, creating an AMVRS peptide linker between the two domains. The resulting expression cassette was PCR-extracted and further ligated in pLV-EF1-MCS lentiviral expression plasmid downstream of the human EF1α promoter by blunt ligation. Viral derived vectors were produced by Vectalys (Labège, France) and used to transduce CHO-S cells, further cultured in CD-CHO medium containing 10 ml/L HT supplement. IL-15 antagonist was collected from supernatant of 5 days cultures of recombinant CHO-S cells, affinity-purified on protein A sepharose column by GTP Technology (Labège, France), and gel-filtrated on a Superdex G200.

Induction of the Murine Model of Type II Collagen (CII)-Induced Arthritis (CIA)

Male DBA/1 mice (Janvier®) 6-8 wk of age were used in all experiments. CII from bovine tracheal cartilage (Sigma C1188) was dissolved in 0.1M acetic acid at 2 mg/ml at 4° C. overnight. The CII solution was then emulsified using a homogenizer with a small blade with an equal volume of Freund's complete adjuvant (Difco 231131) as previously described (Ruchatz, The Journal of Immunology, 1998, 160: 5654-5660). To induce CIA, 200 μg of CII was injected intradermally at the base of the tail of DBA/1 mice. Twenty-one days after immunization, the animals were challenged with 200 μg of CII i.p. in acetic acid 0.05M.

Treatment of Animals

After immunization and subsequent challenge with CII, starting at day 22, animals were divided into two groups: each group received a daily i.p. injection at 1.5 μg/injection/day for 2 weeks of either IgG2a (eBioscience 14-4724) or IL-15AN-Fc fusion protein. Mice were evaluated every day for signs of arthritis based on the following criteria: grade 0, normal joints and no swelling; grade 1, mild swelling and/or erythema; grade 2, pronounced edema or redness of the paw or several digits; and grade 3, severe swelling of entire paw and/or ankylosis. As each limb was individually graded, the maximal clinical score for each mouse was 12.

Treatment of Animals with Established Arthritis

DBA/1 mice were immunized and challenged with CII as described above and monitored every day for signs of arthritis based on the following criteria: grade 0, normal joints and no swelling; grade 1, mild swelling and/or erythema; grade 2, pronounced edema or redness of the paw or several digits; grade 3, severe swelling of entire paw; and grade 4, ankylosis. When animals developed overt arthritis with a minimal clinical score of 1, they were randomly assigned to treatment groups and given either IgG2a or IL-15AN-Fc fusion protein (1.5 μg/injection/day) for 14 consecutive days. Only animals developing arthritis were included in the analysis.

Flow Cytometric Analysis of In Vivo NK and CD8+ Cells

Spleen NK and CD8+ T cells were determined by using a FACS Calibur flow cytometer (Becton Dickinson) 1 h after the last i.p. injection of IL-15AN-Fc or IgG2A (day 35). The mouse splenocytes were incubated with saturating amounts (1 μg/$10^6$ cells) of either FITC-conjugated anti-mouse CD3e mAb, APC-conjugated anti-mouse NKp46 mAb, FITC-conjugated anti-mouse CD11b mAb and phycoerythrin(PE)-conjugated anti-mouse CD27 (BD Pharmingen), or FITC-conjugated anti-mouse CD3e mAb, APC-conjugated anti-mouse CD8 mAb, PE-conjugated anti-mouse CD122 mAb and FITC-conjugated anti-mouse CD44 mAb. Data were processed using FlowJo soft-ware (BD Biosciences).

Histology

Paws were removed postmortem, fixed in 1% paraformaldehyde for 3 days, and decalcified in 5% EDTA for 2 wk before being embedded in paraffin for sectioning. Serial sagittal sections were made, mounted on glass slides, and stained with H&E. Tissue sections were analyzed by light microscopy.

Results

Generation of IL-15AN-Fc

To obtain a specific IL-15 antagonist for preclinical studies, the sequence corresponding to human IL15 was cloned into an expressing vector (GTP Technology, Labège, France) and expressed in CHO-S cells, after being mutated, optimized and linked to a mouse engineered IgG2a Fc region. IL-15 antagonist-IgG2a protein was extracted and purified by protein A sepharose affinity chromatography. Its analysis showed a 97% pure protein which eluted in a gel filtration column as a single and homogenous peak of apparent 260 kDa. This higher than expected size maybe due to an atypic behaviour of the glycosylated protein or to the presence of dimers of Fc-dimers. In vitro antagonist activity of the purified protein in a CTLL2 proliferation assay, induced with 10 pM IL-15, showed total inhibition with a half maximal concentration (IC50) of 2.5 nM (not shown).

Treatment with IL-15AN-Fc Decreased the Severity of CIA

Figure 1D:
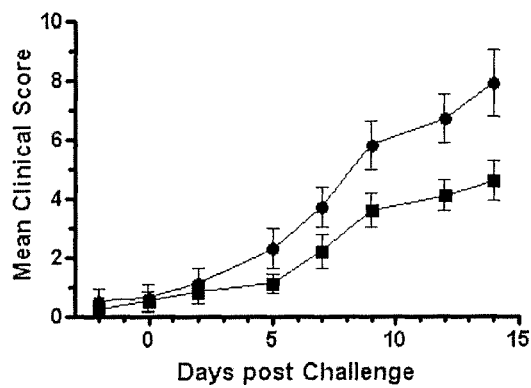
Figure 3A:
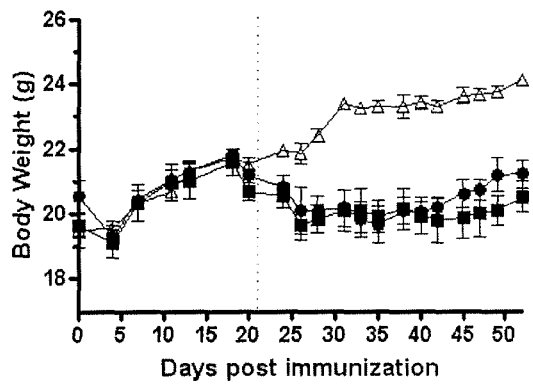
Figure 3B:
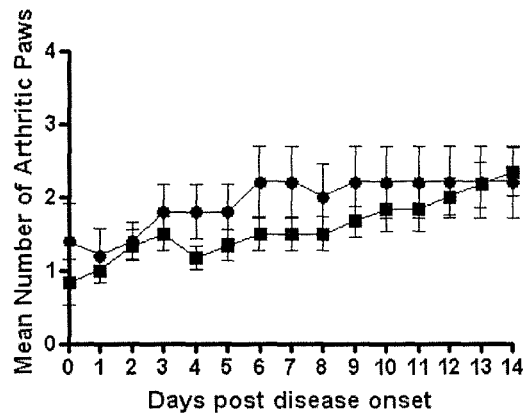
Figure 3C:
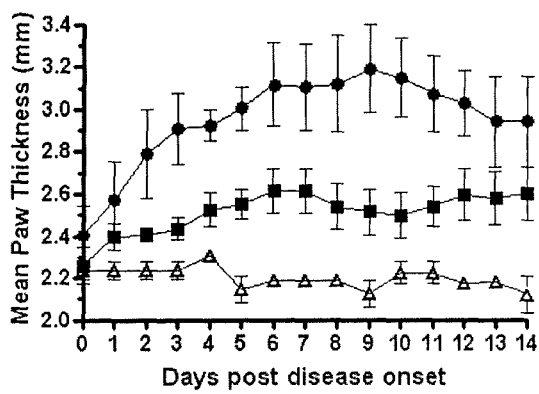
Figure 3D:
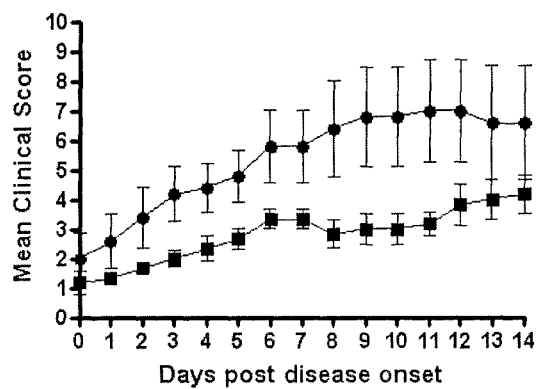

Mice injected intradermally with type II collagen in Freund's complete adjuvant developed severe arthritis when challenged i.p. 21 days later with collagen. The joints affected exhibited prominent swelling and edema, eventually resulting in restricted mobility and ankylosis. The incidence of the disease was accompanied with a loss of body weight which began just after the collagen challenge, and went on for about 2 weeks, after what, mice body weight heightened (FIG. 1A and FIG. 3A). The severity of the disease development was markedly reduced in mice that received daily i.p. injections of 1.5 µg of IL-15AN-Fc beginning on the day after collagen challenge in comparison with controls which received IgG2a. The effect of IL-15AN-Fc was particularly obvious on the mean of paw thickness (FIG. 1C) but also visible although not significant on the mean clinical score (FIG. 1D). Two weeks of daily treatment with IL-15AN-Fc did not affect the percentages of total and mature NKp46+ CD3− CD11b+ CD27− NK cells as well as total $CD8^+$ and memory $CD8^+$ $CD44^+$ $CD122^+$ cells in the spleen of mice (FIG. 2).

Therapeutic Effect of IL-15AN-Fc Treatment on Ongoing CIA

To determine the efficacy of IL-15AN-Fc on disease progression in mice with already established arthritis, treatment of immunized animals was started only when mice developed overt arthritis with a mean clinical score of at least 1 (mean clinical score, 1.2±0.4 and 2.0±0.9, respectively for IL-15AN-Fc and IgG2a groups), and mice then received either IgG2a or IL-15AN-Fc (1.5 µg/day) i.p. for 14 days. As shown on FIGS. 3C and D, treatment with control IgG2a did not affect the progression of arthritis. In contrast, treatment with IL-15AN-Fc limited disease progression during the course of treatment and after (not shown). This therapeutic effect was highly significant (Mann Whitney test, $p<0.001$).

EXAMPLE 2

Material and Methods
Mouse:
C57BL/6 (JANVIER LABS) of 8 weeks were used.
Pharmacokinetic of IL-15AN-Fc In Vivo:
The half-life of IL-15AN-Fc was evaluated in male C57BL/6 mice after a single intravenous injection of 10 mg of IL-15AN-Fc. At each time point, the blood was collected (three mice/point), centrifuged and the plasma was stored at −20° C. IL-15AN-Fc concentration was determined by ELISA. Pharmacokinetic parameters were calculated using a one-compartment model: $Ae^{-Bx}$, A is the initial concentration of IL-15AN-Fc (10 µg) and B was determined with GraphPad Prism software. The half-life $T_{1/2}=Ln(2)/B$.

ELISA Assay:

To determine the amount of IL-15AN-Fc in the plasma. An Fc-IL-15Rα (R&D system) at the concentration of 1.25 µg/ml was used as a capture molecule. The plate was saturated with PBS-tween 5% milk during 1 h. After washing, serum was added for 2 h at room temperature. An HRP Goat Anti-mouse IgG(H+L) diluted at 250 ng/mL (INTERCHIM) directed against the Fc was added for 1 h. After washing, TMB (INTERCHIM) substrate solution was finally added and the absorbance was measured by spectrophotometry (450 nm). A standard range with IL-15AN-Fc was performed in parallel.

Effect of IL-15AN-Fc on NK and T Cells Homeostasis:

To determine whether IL-15AN-Fc has an effect on the development of NK and T cells in the steady state, three groups (3 mice/group) of male C57BL/6 mice were injected intraperitoneally with different doses of IL-15AN-Fc (1.5, 5 and 25 µg), once per day and were sacrificed at day 5. Spleens were collected and NK (FITC hamster anti-mouse CD3 from BD Biosciencs and APC anti-mouse NK1.1 from e-Bioscience) and $CD8^+$ T cell (FITC hamster anti-mouse CD3 from BD Biosciences and APC anti-mouse CD8α from e-Bioscience) populations were determined by flow cytometry CALIBUR and the data analysed by FlowJo software.

Results

IL-15AN-Fc has a half-life of about 12 hours in vivo (FIG. 4). Its injection for four days at different concentration had no effect on mice NK and CD8+ T cells homeostasis (FIG. 5).

REFERENCES

Throughout this application, various references describe the state of the art to which this invention pertains. The disclosures of these references are hereby incorporated by reference into the present disclosure.

The invention claimed is:

1. A method of treating an inflammatory or autoimmune disease associated with IL-15 in a patient in need thereof, comprising administering to said patient a therapeutically effective amount of an IL-15 antagonist selected from:
   an IL-15 mutant polypeptide which amino acid sequence is identical to the sequence in SEQ ID NO:1 except the leucine residue at position 45 is substituted by an aspartic acid residue, the asparagine residue at position 65 is substituted by a lysine residue, and the leucine residue at position 69 is substituted by an arginine residue; and
   a fusion protein comprising the IL-15 mutant polypeptide fused to a heterologous polypeptide, or a dimer thereof.

2. The method according to claim 1 wherein the inflammatory or autoimmune disease is selected from the group consisting of a rheumatic disease, systemic lupus erythematosus, Sjogren's syndrome, scleroderma, mixed connective tissue disease, dermatomyositis, polymyositis, Reiter's syndrome or Behcet's disease, diabetes, an autoimmune disease of the thyroid, an autoimmune disease of the central nervous system, phemphigus, psoriasis, and inflammatory bowel disease.

3. The method of claim 2, wherein the rheumatic disease is rheumatoid arthritis.

4. The method of claim 2, wherein the autoimmune disease of the thyroid is Hashimoto's thyroiditis or Graves' Disease.

5. The method of claim 2, wherein the autoimmune disease of the central nervous system is selected from the group consisting of multiple sclerosis, myasthenia gravis and encephalomyelitis.

6. The method of claim 2, wherein the said phemphigus is selected from the group consisting of phemphigus vulgaris, phemphigus vegetans, phemphigus foliaceus, Senear-Usher syndrome and Brazilian phemphigus.

7. The method of claim 2, wherein the inflammatory bowel disease is ulcerative colitis or Crohn's Disease.

8. The method of claim 1, wherein the heterologous polypeptide is an immunoglobulin constant domain.

9. The method of claim 8, wherein the immunoglobulin constant domain is obtained from an immunoglobulin selected from the group consisting of IgG-1, IgG-2, IgG-3, IgG-4, IgA, IgE, IgD and IgM.

10. The method of claim 8, wherein the immunoglobulin constant domain is a Fc region.

11. The method of claim 8, wherein the IL-15 mutant polypeptide and the immunoglobulin constant domain are linked by a linker.

12. The method of claim 11, wherein the linker has 4; 5; 6; 7; 8; 9; 10; 11; 12; 13; 14; 15; 16; 17; 18; 19; 20; 21; 22; 23; 24; 25; 26; 27; 28; 29; or 30 amino acid residues.

13. The method of claim 11, wherein the linker is selected from the group consisting of SEQ ID NO:10, SEQ ID NO:11, SEQ ID NO:12, SEQ ID NO:13, SEQ ID NO:14 and SEQ ID NO:15.

14. The method of claim 1, wherein the IL-15 mutant polypeptide has an amino acid sequence selected from the group consisting of SEQ ID NO:2, SEQ ID NO:3, SEQ ID NO:4, SEQ ID NO:7, SEQ ID NO:8 and SEQ ID NO:9.

15. A method of treating inflammation associated with IL-15 in a transplant patient in need thereof, comprising administering to said patient a therapeutically effective amount of an IL-15 antagonist selected from:
   an IL-15 mutant polypeptide which amino acid sequence is identical to the sequence in SEQ ID NO:1 except the leucine residue at position 45 is substituted by an aspartic acid residue, the asparagine residue at position 65 is substituted by a lysine residue, and the leucine residue at position 69 is substituted by an arginine residue; and
   a fusion protein comprising the IL-15 mutant polypeptide fused to a heterologous polypeptide, or a dimer thereof.

16. The method of claim 15, wherein the transplant patient has graft versus host disease.

* * * * *

SEQUENCE LISTING

<160> NUMBER OF SEQ ID NOS: 15

<210> SEQ ID NO 1
<211> LENGTH: 114
<212> TYPE: PRT
<213> ORGANISM: Homo sapiens

<400> SEQUENCE: 1

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile

```
                85                  90                  95
Lys Glu Phe Leu Gln Ser Phe Val His Ile Val Gln Met Phe Ile Asn
            100                 105                 110

Thr Ser

<210> SEQ ID NO 2
<211> LENGTH: 337
<212> TYPE: PRT
<213> ORGANISM: Artificial
<220> FEATURE:
<223> OTHER INFORMATION: Synthetic fusion protien IL-15-IgG1Fc (Murine)

<400> SEQUENCE: 2

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Asp Glu Leu Gln
        35                  40                  45

Val Ile Ser Leu Glu Ser Gly Asp Ala Ser Ile His Asp Thr Val Glu
    50                  55                  60

Lys Leu Ile Ile Arg Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser Ser Gly Cys Lys Pro Cys Ile Cys Thr Val Pro Glu Val Ser
        115                 120                 125

Ser Val Phe Ile Phe Pro Pro Lys Pro Lys Asp Val Leu Thr Ile Thr
    130                 135                 140

Leu Thr Pro Lys Val Thr Cys Val Val Val Asp Ile Ser Lys Asp Asp
145                 150                 155                 160

Pro Glu Val Gln Phe Ser Trp Phe Val Asp Asp Val Glu Val His Thr
                165                 170                 175

Ala Gln Thr Gln Pro Arg Glu Glu Gln Phe Asn Ser Thr Phe Arg Ser
            180                 185                 190

Val Ser Glu Leu Pro Ile Met His Gln Asp Trp Leu Asn Gly Lys Glu
        195                 200                 205

Phe Lys Cys Arg Val Asn Ser Ala Ala Phe Pro Ala Pro Ile Glu Lys
    210                 215                 220

Thr Ile Ser Lys Thr Lys Gly Arg Pro Lys Ala Pro Gln Val Tyr Thr
225                 230                 235                 240

Ile Pro Pro Pro Lys Glu Gln Met Ala Lys Asp Lys Val Ser Leu Thr
                245                 250                 255

Cys Met Ile Thr Asp Phe Phe Pro Glu Asp Ile Thr Val Glu Trp Gln
            260                 265                 270

Trp Asn Gly Gln Pro Ala Glu Asn Tyr Lys Asn Thr Gln Pro Ile Met
        275                 280                 285

Asp Thr Asp Gly Ser Tyr Phe Val Tyr Ser Lys Leu Asn Val Gln Lys
    290                 295                 300

Ser Asn Trp Glu Ala Gly Asn Thr Phe Thr Cys Ser Val Leu His Glu
305                 310                 315                 320

Gly Leu His Asn His His Thr Glu Lys Ser Leu Ser His Ser Pro Gly
                325                 330                 335
```

Lys

<210> SEQ ID NO 3
<211> LENGTH: 341
<212> TYPE: PRT
<213> ORGANISM: Artificial
<220> FEATURE:
<223> OTHER INFORMATION: Synthetic fusion protein IL-15-IgG1Fc (Human)

<400> SEQUENCE: 3

```
Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Asp Glu Leu Gln
        35                  40                  45

Val Ile Ser Leu Glu Ser Gly Asp Ala Ser Ile His Asp Thr Val Glu
    50                  55                  60

Lys Leu Ile Ile Arg Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser Asp Lys Thr His Thr Cys Pro Pro Cys Pro Ala Pro Glu Leu
        115                 120                 125

Leu Gly Gly Pro Ser Val Phe Leu Phe Pro Pro Lys Pro Lys Asp Thr
    130                 135                 140

Leu Met Ile Ser Arg Thr Pro Glu Val Thr Cys Val Val Val Asp Val
145                 150                 155                 160

Ser His Glu Asp Pro Glu Val Lys Phe Asn Trp Tyr Val Asp Gly Val
                165                 170                 175

Glu Val His Asn Ala Lys Thr Lys Pro Arg Glu Glu Gln Tyr Asn Ser
            180                 185                 190

Thr Tyr Arg Val Val Ser Val Leu Thr Val Leu His Gln Asp Trp Leu
        195                 200                 205

Asn Gly Lys Glu Tyr Lys Cys Lys Val Ser Asn Lys Ala Leu Pro Ala
    210                 215                 220

Pro Ile Glu Lys Thr Ile Ser Lys Ala Lys Gly Gln Pro Arg Glu Pro
225                 230                 235                 240

Gln Val Tyr Thr Leu Pro Pro Ser Arg Glu Glu Met Thr Lys Asn Gln
                245                 250                 255

Val Ser Leu Thr Cys Leu Val Lys Gly Phe Tyr Pro Ser Asp Ile Ala
            260                 265                 270

Val Glu Trp Glu Ser Asn Gly Gln Pro Glu Asn Asn Tyr Lys Thr Thr
        275                 280                 285

Pro Pro Val Leu Asp Ser Asp Gly Ser Phe Phe Leu Tyr Ser Lys Leu
    290                 295                 300

Thr Val Asp Lys Ser Arg Trp Gln Gln Gly Asn Val Phe Ser Cys Ser
305                 310                 315                 320

Val Met His Glu Ala Leu His Asn His Tyr Thr Gln Lys Ser Leu Ser
                325                 330                 335

Leu Ser Pro Gly Lys
            340
```

<210> SEQ ID NO 4
<211> LENGTH: 337
<212> TYPE: PRT
<213> ORGANISM: Artificial
<220> FEATURE:
<223> OTHER INFORMATION: Synthetic fusion protein IL-15-IgG2Fc (Human)

<400> SEQUENCE: 4

```
Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Asp Glu Leu Gln
        35                  40                  45

Val Ile Ser Leu Glu Ser Gly Asp Ala Ser Ile His Asp Thr Val Glu
    50                  55                  60

Lys Leu Ile Ile Arg Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser Val Glu Cys Pro Pro Cys Pro Ala Pro Pro Val Ala Gly Pro
        115                 120                 125

Ser Val Phe Leu Phe Pro Pro Lys Pro Lys Asp Thr Leu Met Ile Ser
    130                 135                 140

Arg Thr Pro Glu Val Thr Cys Val Val Val Asp Val Ser His Glu Asp
145                 150                 155                 160

Pro Glu Val Gln Phe Asn Trp Tyr Val Asp Gly Met Glu Val His Asn
                165                 170                 175

Ala Lys Thr Lys Pro Arg Glu Glu Gln Phe Asn Ser Thr Phe Arg Val
            180                 185                 190

Val Ser Val Leu Thr Val Val His Gln Asp Trp Leu Asn Gly Lys Glu
        195                 200                 205

Tyr Lys Cys Lys Val Ser Asn Lys Gly Leu Pro Ala Pro Ile Glu Lys
    210                 215                 220

Thr Ile Ser Lys Thr Lys Gly Gln Pro Arg Glu Pro Gln Val Tyr Thr
225                 230                 235                 240

Leu Pro Pro Ser Arg Glu Glu Met Thr Lys Asn Gln Val Ser Leu Thr
                245                 250                 255

Cys Leu Val Lys Gly Phe Tyr Pro Ser Asp Ile Ala Val Glu Trp Glu
            260                 265                 270

Ser Asn Gly Gln Pro Glu Asn Asn Tyr Lys Thr Thr Pro Pro Met Leu
        275                 280                 285

Asp Ser Asp Gly Ser Phe Phe Leu Tyr Ser Lys Leu Thr Val Asp Lys
    290                 295                 300

Ser Arg Trp Gln Gln Gly Asn Val Phe Ser Cys Ser Val Met His Glu
305                 310                 315                 320

Ala Leu His Asn His Tyr Thr Gln Lys Ser Leu Ser Leu Ser Pro Gly
                325                 330                 335

Lys
```

<210> SEQ ID NO 5
<211> LENGTH: 32
<212> TYPE: DNA

```
<213> ORGANISM: Artificial
<220> FEATURE:
<223> OTHER INFORMATION: Synthetic oligonucleotide primer

<400> SEQUENCE: 5
ctccttgatg ttcttctcct ccagttcctc ac                              32

<210> SEQ ID NO 6
<211> LENGTH: 39
<212> TYPE: DNA
<213> ORGANISM: Artificial
<220> FEATURE:
<223> OTHER INFORMATION: Synthetic oligonucleotide primer

<400> SEQUENCE: 6
ttcctgcaga gcttcgtaca tattgtccaa atgttcatc                       39

<210> SEQ ID NO 7
<211> LENGTH: 352
<212> TYPE: PRT
<213> ORGANISM: Artificial
<220> FEATURE:
<223> OTHER INFORMATION: Synthetic fusion protein IL-15- Linker-IgG1Fc

<400> SEQUENCE: 7
```

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
                20                  25                  30

Pro Ser Cys Lys Val Thr Ala Met Lys Cys Phe Leu Asp Glu Leu Gln
            35                  40                  45

Val Ile Ser Leu Glu Ser Gly Asp Ala Ser Ile His Asp Thr Val Glu
        50                  55                  60

Lys Leu Ile Ile Arg Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser Gly Gly Gly Gly Ser Gly Gly Gly Gly Ser Gly Gly Gly Gly
        115                 120                 125

Ser Ser Gly Cys Lys Pro Cys Ile Cys Thr Val Pro Glu Val Ser Ser
    130                 135                 140

Val Phe Ile Phe Pro Pro Lys Pro Lys Asp Val Leu Thr Ile Thr Leu
145                 150                 155                 160

Thr Pro Lys Val Thr Cys Val Val Val Asp Ile Ser Lys Asp Asp Pro
                165                 170                 175

Glu Val Gln Phe Ser Trp Phe Val Asp Asp Val Glu Val His Thr Ala
            180                 185                 190

Gln Thr Gln Pro Arg Glu Glu Gln Phe Asn Ser Thr Phe Arg Ser Val
        195                 200                 205

Ser Glu Leu Pro Ile Met His Gln Asp Trp Leu Asn Gly Lys Glu Phe
    210                 215                 220

Lys Cys Arg Val Asn Ser Ala Ala Phe Pro Ala Pro Ile Glu Lys Thr
225                 230                 235                 240

Ile Ser Lys Thr Lys Gly Arg Pro Lys Ala Pro Gln Val Tyr Thr Ile
                245                 250                 255

Pro Pro Pro Lys Glu Gln Met Ala Lys Asp Lys Val Ser Leu Thr Cys

```
                260                 265                 270
Met Ile Thr Asp Phe Phe Pro Glu Asp Ile Thr Val Glu Trp Gln Trp
            275                 280                 285

Asn Gly Gln Pro Ala Glu Asn Tyr Lys Asn Thr Gln Pro Ile Met Asp
        290                 295                 300

Thr Asp Gly Ser Tyr Phe Val Tyr Ser Lys Leu Asn Val Gln Lys Ser
305                 310                 315                 320

Asn Trp Glu Ala Gly Asn Thr Phe Thr Cys Ser Val Leu His Glu Gly
                325                 330                 335

Leu His Asn His His Thr Glu Lys Ser Leu Ser His Ser Pro Gly Lys
                340                 345                 350

<210> SEQ ID NO 8
<211> LENGTH: 356
<212> TYPE: PRT
<213> ORGANISM: Artificial
<220> FEATURE:
<223> OTHER INFORMATION: Synthetic fusion protein IL-15- Linker - IgG1Fc

<400> SEQUENCE: 8

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Asp Glu Leu Gln
        35                  40                  45

Val Ile Ser Leu Glu Ser Gly Asp Ala Ser Ile His Asp Thr Val Glu
    50                  55                  60

Lys Leu Ile Ile Arg Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser Gly Gly Gly Gly Ser Gly Gly Gly Gly Ser Gly Gly Gly Gly
        115                 120                 125

Ser Asp Lys Thr His Thr Cys Pro Pro Cys Pro Ala Pro Glu Leu Leu
    130                 135                 140

Gly Gly Pro Ser Val Phe Leu Phe Pro Pro Lys Pro Lys Asp Thr Leu
145                 150                 155                 160

Met Ile Ser Arg Thr Pro Glu Val Thr Cys Val Val Val Asp Val Ser
                165                 170                 175

His Glu Asp Pro Glu Val Lys Phe Asn Trp Tyr Val Asp Gly Val Glu
            180                 185                 190

Val His Asn Ala Lys Thr Lys Pro Arg Glu Glu Gln Tyr Asn Ser Thr
        195                 200                 205

Tyr Arg Val Val Ser Val Leu Thr Val Leu His Gln Asp Trp Leu Asn
    210                 215                 220

Gly Lys Glu Tyr Lys Cys Lys Val Ser Asn Lys Ala Leu Pro Ala Pro
225                 230                 235                 240

Ile Glu Lys Thr Ile Ser Lys Ala Lys Gly Gln Pro Arg Glu Pro Gln
                245                 250                 255

Val Tyr Thr Leu Pro Pro Ser Arg Glu Glu Met Thr Lys Asn Gln Val
            260                 265                 270

Ser Leu Thr Cys Leu Val Lys Gly Phe Tyr Pro Ser Asp Ile Ala Val
```

```
                275                 280                 285
Glu Trp Glu Ser Asn Gly Gln Pro Glu Asn Asn Tyr Lys Thr Thr Pro
        290                 295                 300
Pro Val Leu Asp Ser Asp Gly Ser Phe Phe Leu Tyr Ser Lys Leu Thr
305                 310                 315                 320
Val Asp Lys Ser Arg Trp Gln Gln Gly Asn Val Phe Ser Cys Ser Val
                325                 330                 335
Met His Glu Ala Leu His Asn His Tyr Thr Gln Lys Ser Leu Ser Leu
            340                 345                 350
Ser Pro Gly Lys
        355

<210> SEQ ID NO 9
<211> LENGTH: 352
<212> TYPE: PRT
<213> ORGANISM: Artificial
<220> FEATURE:
<223> OTHER INFORMATION: Synthetic fusion protein IL-15- Linker - IgG2Fc

<400> SEQUENCE: 9

Asn Trp Val Asn Val Ile Ser Asp Leu Lys Lys Ile Glu Asp Leu Ile
1               5                   10                  15
Gln Ser Met His Ile Asp Ala Thr Leu Tyr Thr Glu Ser Asp Val His
            20                  25                  30
Pro Ser Cys Lys Val Thr Ala Met Lys Cys Phe Leu Asp Glu Leu Gln
        35                  40                  45
Val Ile Ser Leu Glu Ser Gly Asp Ala Ser Ile His Asp Thr Val Glu
    50                  55                  60
Lys Leu Ile Ile Arg Ala Asn Asn Ser Leu Ser Ser Asn Gly Asn Val
65                  70                  75                  80
Thr Glu Ser Gly Cys Lys Glu Cys Glu Glu Leu Glu Glu Lys Asn Ile
                85                  90                  95
Lys Glu Phe Leu Gln Ser Phe Val His Ile Val Gln Met Phe Ile Asn
            100                 105                 110
Thr Ser Gly Gly Gly Gly Ser Gly Gly Gly Gly Ser Gly Gly Gly Gly
        115                 120                 125
Ser Val Glu Cys Pro Pro Cys Pro Ala Pro Pro Val Ala Gly Pro Ser
    130                 135                 140
Val Phe Leu Phe Pro Pro Lys Pro Lys Asp Thr Leu Met Ile Ser Arg
145                 150                 155                 160
Thr Pro Glu Val Thr Cys Val Val Val Asp Val Ser His Glu Asp Pro
                165                 170                 175
Glu Val Gln Phe Asn Trp Tyr Val Asp Gly Met Glu Val His Asn Ala
            180                 185                 190
Lys Thr Lys Pro Arg Glu Glu Gln Phe Asn Ser Thr Phe Arg Val Val
        195                 200                 205
Ser Val Leu Thr Val Val His Gln Asp Trp Leu Asn Gly Lys Glu Tyr
    210                 215                 220
Lys Cys Lys Val Ser Asn Lys Gly Leu Pro Ala Pro Ile Glu Lys Thr
225                 230                 235                 240
Ile Ser Lys Thr Lys Gly Gln Pro Arg Glu Pro Gln Val Tyr Thr Leu
                245                 250                 255
Pro Pro Ser Arg Glu Glu Met Thr Lys Asn Gln Val Ser Leu Thr Cys
            260                 265                 270
Leu Val Lys Gly Phe Tyr Pro Ser Asp Ile Ala Val Glu Trp Glu Ser
```

```
                    275                 280                 285

Asn Gly Gln Pro Glu Asn Asn Tyr Lys Thr Thr Pro Pro Met Leu Asp
    290                 295                 300

Ser Asp Gly Ser Phe Phe Leu Tyr Ser Lys Leu Thr Val Asp Lys Ser
305                 310                 315                 320

Arg Trp Gln Gln Gly Asn Val Phe Ser Cys Ser Val Met His Glu Ala
                325                 330                 335

Leu His Asn His Tyr Thr Gln Lys Ser Leu Ser Leu Ser Pro Gly Lys
            340                 345                 350

<210> SEQ ID NO 10
<211> LENGTH: 15
<212> TYPE: PRT
<213> ORGANISM: Artificial
<220> FEATURE:
<223> OTHER INFORMATION: Synthetic linker peptide

<400> SEQUENCE: 10

Gly Gly Gly Gly Ser Gly Gly Gly Gly Ser Gly Gly Gly Gly Ser
1               5                   10                  15

<210> SEQ ID NO 11
<211> LENGTH: 20
<212> TYPE: PRT
<213> ORGANISM: Artificial
<220> FEATURE:
<223> OTHER INFORMATION: Synthetic linker peptide

<400> SEQUENCE: 11

Gly Gly Gly Gly Ser Gly Gly Gly Gly Ser Gly Gly Gly Gly Ser Gly
1               5                   10                  15

Gly Gly Gly Ser
            20

<210> SEQ ID NO 12
<211> LENGTH: 5
<212> TYPE: PRT
<213> ORGANISM: Artificial
<220> FEATURE:
<223> OTHER INFORMATION: Synthetic linker peptide

<400> SEQUENCE: 12

Gly Gly Gly Gly Ser
1               5

<210> SEQ ID NO 13
<211> LENGTH: 3
<212> TYPE: PRT
<213> ORGANISM: Artificial
<220> FEATURE:
<223> OTHER INFORMATION: Synthetic linker peptide

<400> SEQUENCE: 13

Gly Gly Ser
1

<210> SEQ ID NO 14
<211> LENGTH: 3
<212> TYPE: PRT
<213> ORGANISM: Artificial
<220> FEATURE:
<223> OTHER INFORMATION: Synthetic linker peptide

<400> SEQUENCE: 14
```

```
Gly Gly Gly
1

<210> SEQ ID NO 15
<211> LENGTH: 15
<212> TYPE: PRT
<213> ORGANISM: Artificial
<220> FEATURE:
<223> OTHER INFORMATION: Synthetic linker peptide

<400> SEQUENCE: 15

Gly Gly Gly Ser Ser Gly Gly Gly Ser Ser Gly Gly Gly Ser Ser
1               5                   10                  15
```